United States Patent
Jensen

(10) Patent No.: US 9,615,889 B2
(45) Date of Patent: *Apr. 11, 2017

(54) SYSTEM FOR IMAGE-BASED ROBOTIC SURGERY

(71) Applicant: MAKO Surgical Corp., Fort Lauderdale, FL (US)

(72) Inventor: Vernon Jensen, Draper, UT (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/994,915

(22) Filed: Jan. 13, 2016

(65) Prior Publication Data
US 2016/0128788 A1     May 12, 2016

Related U.S. Application Data

(63) Continuation of application No. 13/728,756, filed on Dec. 27, 2012, now Pat. No. 9,259,278.
(Continued)

(51) Int. Cl.
*A61B 5/05*      (2006.01)
*A61B 34/30*    (2016.01)
(Continued)

(52) U.S. Cl.
CPC ............... *A61B 34/30* (2016.02); *A61B 6/12* (2013.01); *A61B 6/4405* (2013.01);
(Continued)

(58) Field of Classification Search
CPC ....... A61B 34/30; A61B 34/20; A61B 6/4441; A61B 6/12; A61B 6/487; A61B 6/4405;
(Continued)

(56) References Cited

U.S. PATENT DOCUMENTS 6,131,690 A * 10/2000 Galando ............. A61B 6/4405
                                                          180/19.1
6,526,609 B2   3/2003 Wong
(Continued)

FOREIGN PATENT DOCUMENTS

CN          102256555        11/2011
DE     10 2010 041 201        3/2012
(Continued)

OTHER PUBLICATIONS

International Search Report and Written Opinion for International Application No. PCT/US2012/071792, mailed May 24, 2013, 10 pages.
(Continued)

*Primary Examiner* — Sanjay Cattungal
(74) *Attorney, Agent, or Firm* — Foley & Lardner LLP

(57) ABSTRACT

A robotic surgery system includes a robotic arm fixed relative to an operating room. The robotic arm comprises a mounting fixture configured to be coupled to a first element of a fluoroscopic imaging system, wherein the first element is one of a source element and a detector element. The system further includes a second element of the imaging system, wherein the second element is the other of the source element and the detector element. The second element is configured to be repositionable relative to the first element and relative to a patient tissue structure. The system further includes a controller operatively coupled to the robotic arm, configured to receive signals from a sensing system. The sensing system detects motion of one or more sensor elements coupled to each of the first and second elements and determine a relative spatial positioning between the elements of the fluoroscopic imaging system.

19 Claims, 16 Drawing Sheets

Related U.S. Application Data

(60) Provisional application No. 61/582,145, filed on Dec. 30, 2011.

(51) Int. Cl.
| | | |
|---|---|---|
| *A61B 34/20* | (2016.01) | |
| *A61B 6/00* | (2006.01) | |
| *A61B 6/12* | (2006.01) | |
| *A61B 90/00* | (2016.01) | |

(52) U.S. Cl.
CPC .......... *A61B 6/4441* (2013.01); *A61B 6/4452* (2013.01); *A61B 6/4458* (2013.01); *A61B 6/487* (2013.01); *A61B 34/20* (2016.02); *A61B 6/4464* (2013.01); *A61B 2034/2055* (2016.02); *A61B 2034/2059* (2016.02); *A61B 2034/2061* (2016.02); *A61B 2090/376* (2016.02)

(58) Field of Classification Search
CPC ................ A61B 6/4452; A61B 6/4458; A61B 2090/376; A61B 2034/2059; A61B 2034/2061; A61B 2034/2055; A61B 6/4464
USPC .................................................. 600/407–430
See application file for complete search history.

(56) References Cited

U.S. PATENT DOCUMENTS

| | | | |
|---|---|---|---|
| 6,675,415 B2 | 1/2004 | Wong | |
| 8,252,049 B2* | 8/2012 | Maschke | A61B 6/12 606/108 |
| 8,315,691 B2* | 11/2012 | Sumanaweera | A61N 5/1049 600/407 |
| 8,442,621 B2* | 5/2013 | Gorek | A61B 34/20 600/424 |
| 8,489,176 B1 | 7/2013 | Ben-David et al. | |
| 2002/0090058 A1* | 7/2002 | Yasuda | A61B 6/08 378/205 |
| 2002/0138904 A1* | 10/2002 | Wong | A61B 6/0442 5/600 |
| 2003/0101513 A1 | 6/2003 | Wong | |
| 2003/0120283 A1* | 6/2003 | Stoianovici | A61B 34/70 606/130 |
| 2004/0131150 A1* | 7/2004 | Pankratov | A61N 5/10 378/65 |
| 2005/0054915 A1* | 3/2005 | Sukovic | A61B 6/032 600/424 |
| 2005/0171396 A1* | 8/2005 | Pankratov | A61N 5/1049 600/1 |
| 2005/0207526 A1* | 9/2005 | Altman | A61B 6/032 378/20 |
| 2007/0023669 A1* | 2/2007 | Hefetz | A61B 6/032 250/370.14 |
| 2008/0125649 A1* | 5/2008 | Meyer | A61B 6/0457 600/426 |
| 2010/0114308 A1 | 5/2010 | Maschke | |
| 2010/0170362 A1 | 7/2010 | Bennett et al. | |
| 2011/0276179 A1 | 11/2011 | Banks et al. | |

FOREIGN PATENT DOCUMENTS

| | | |
|---|---|---|
| WO | WO-00/64367 | 11/2000 |
| WO | WO-2006/042211 | 4/2006 |
| WO | WO-2010/044852 | 4/2010 |

OTHER PUBLICATIONS

Extended European Search Report for EP Application No. 16151245.4, mail date Apr. 15, 2016, 7 pages.

\* cited by examiner

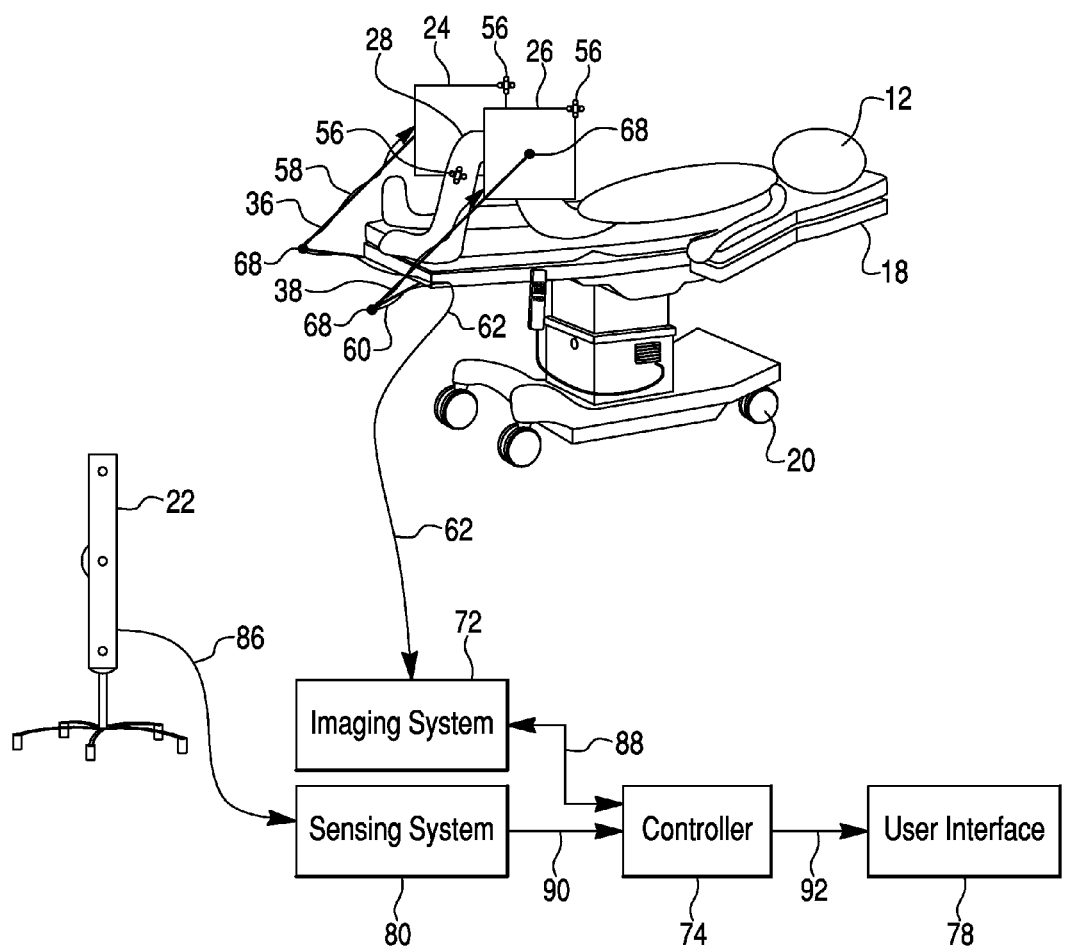

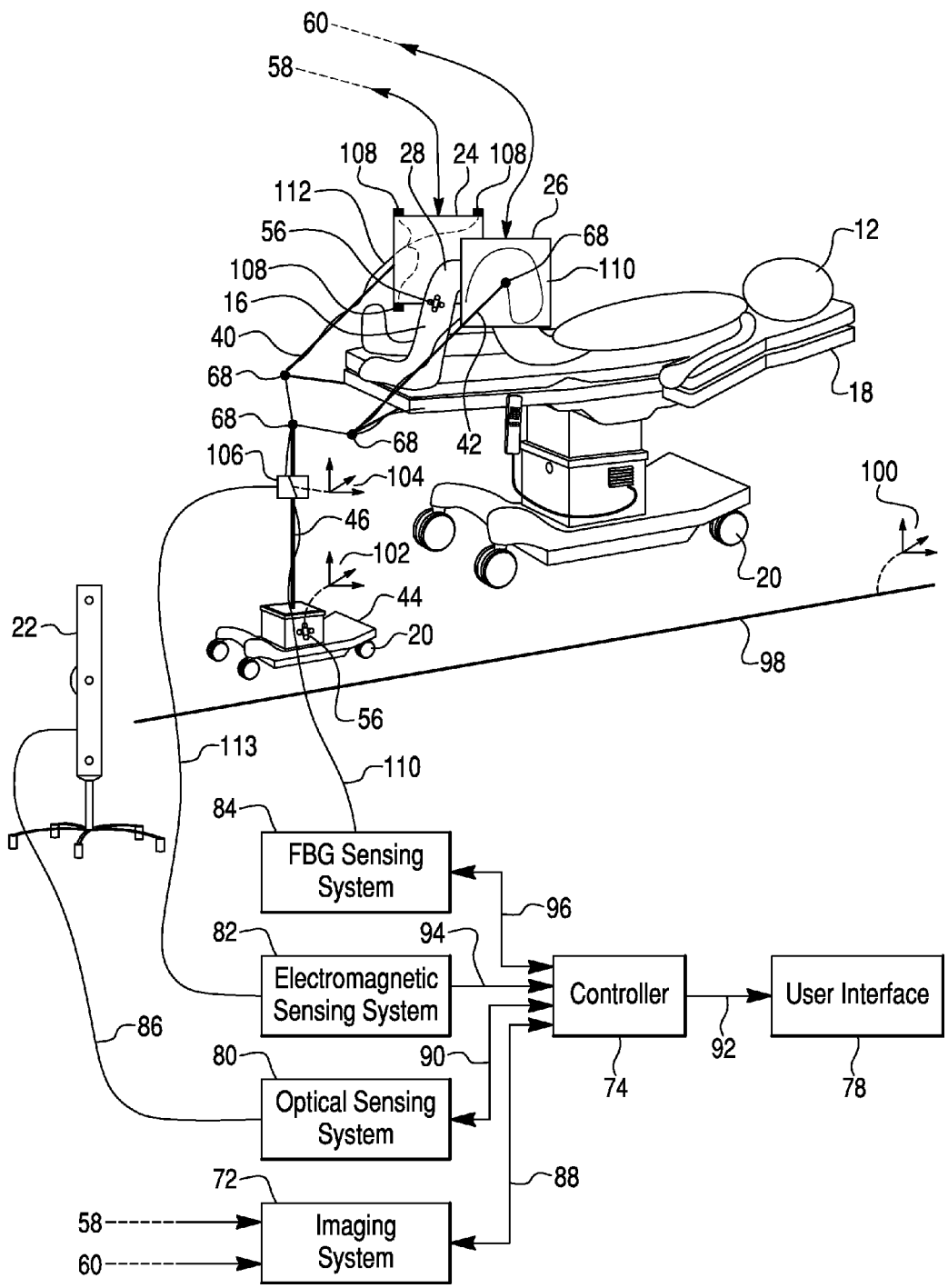

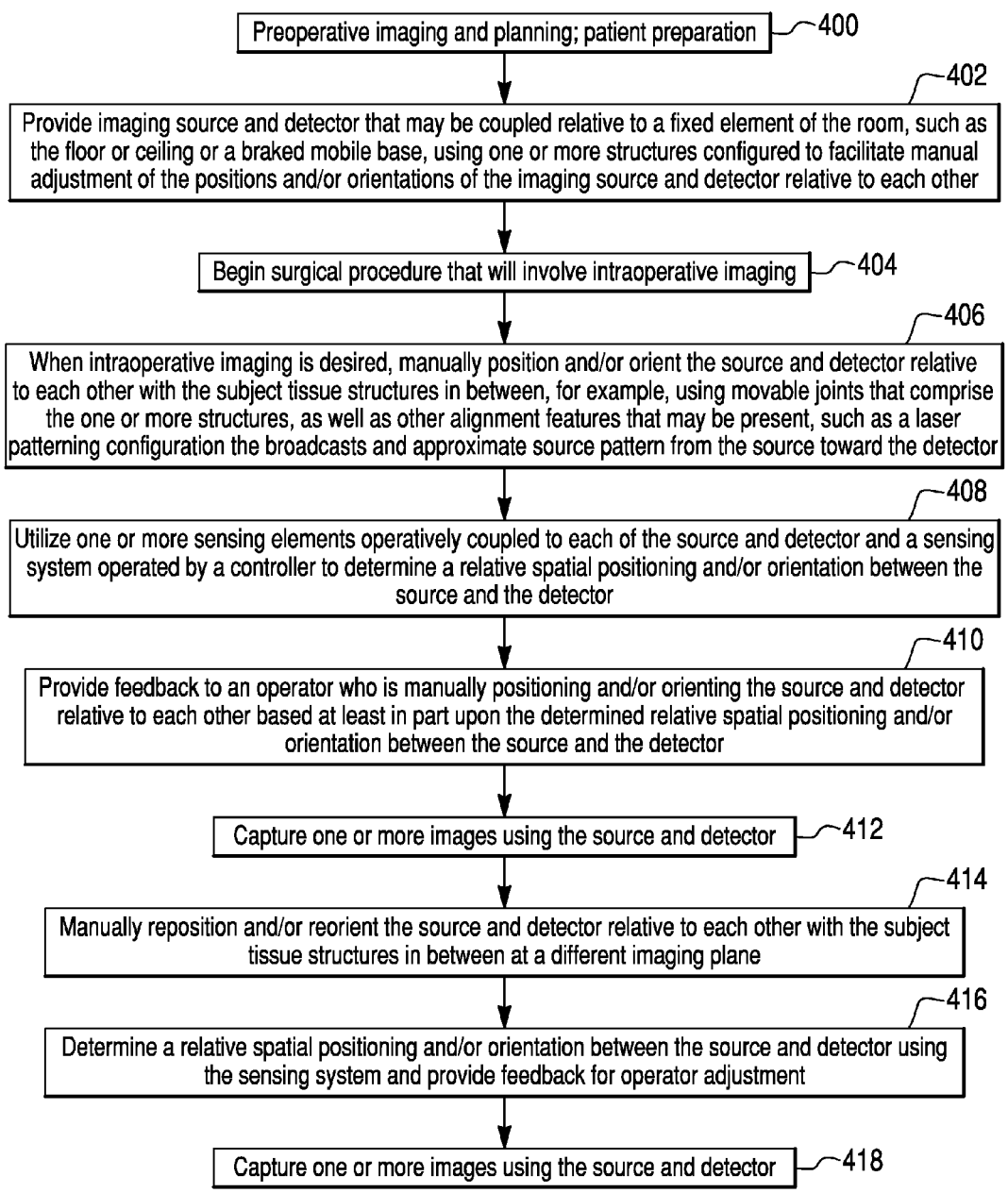

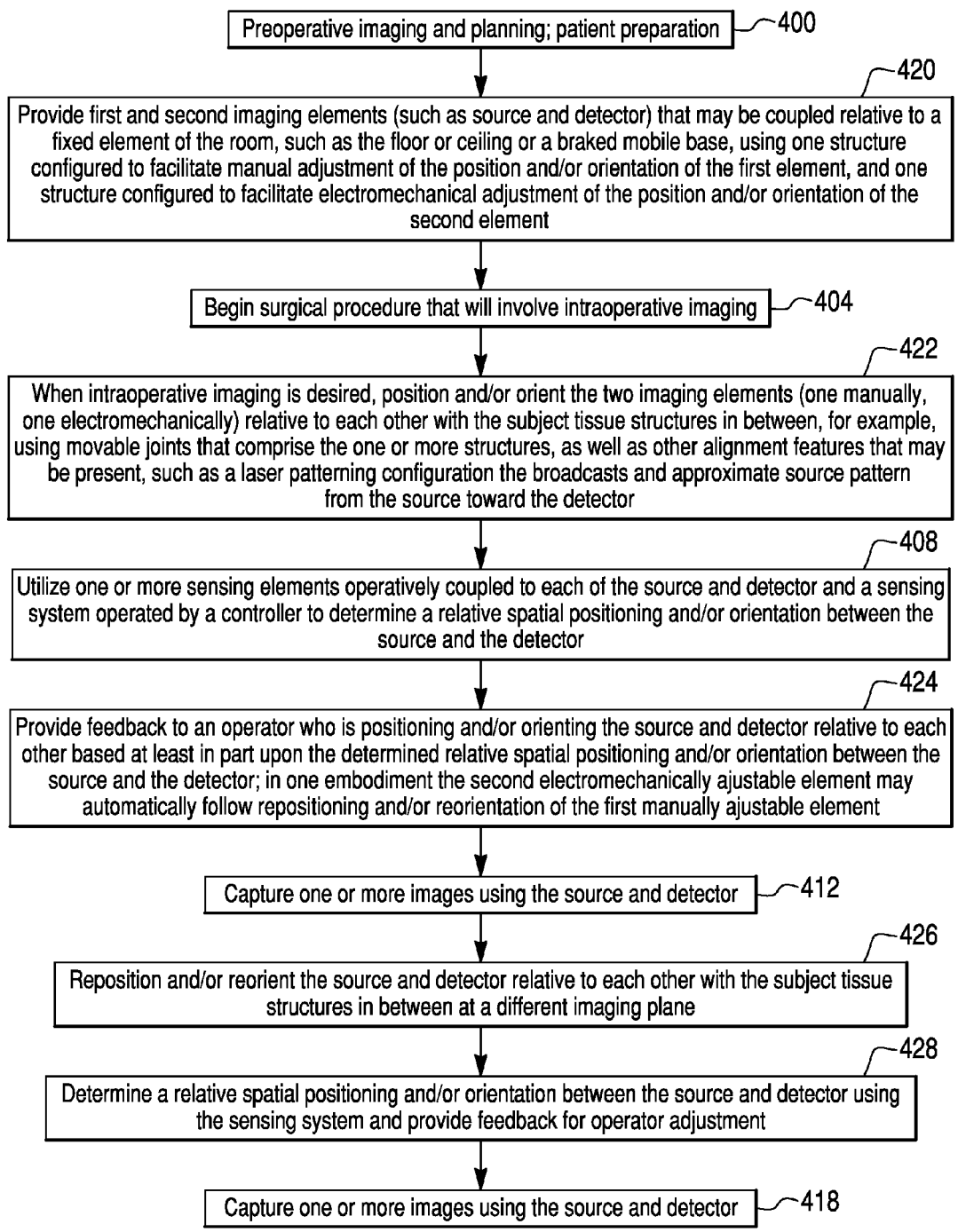

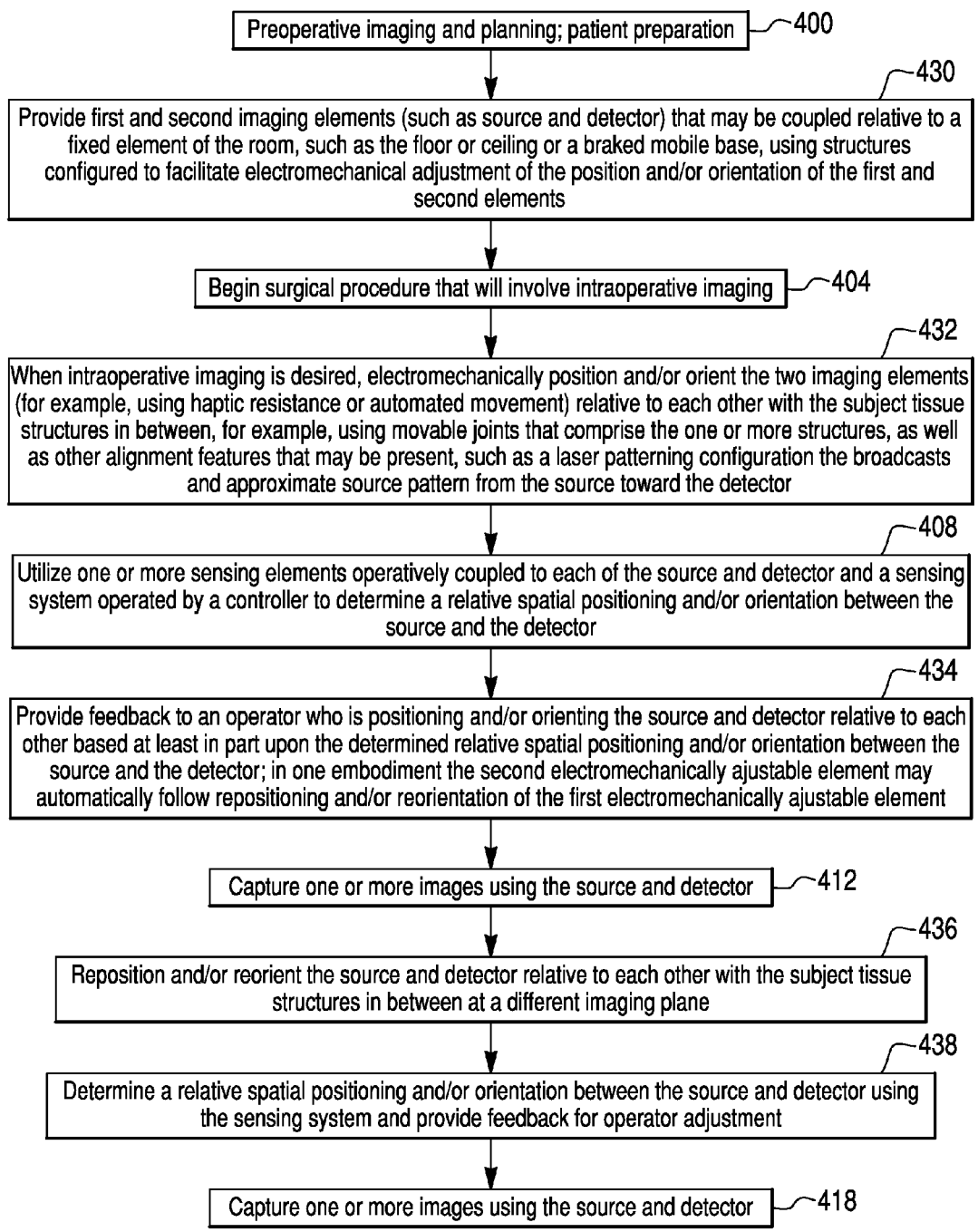

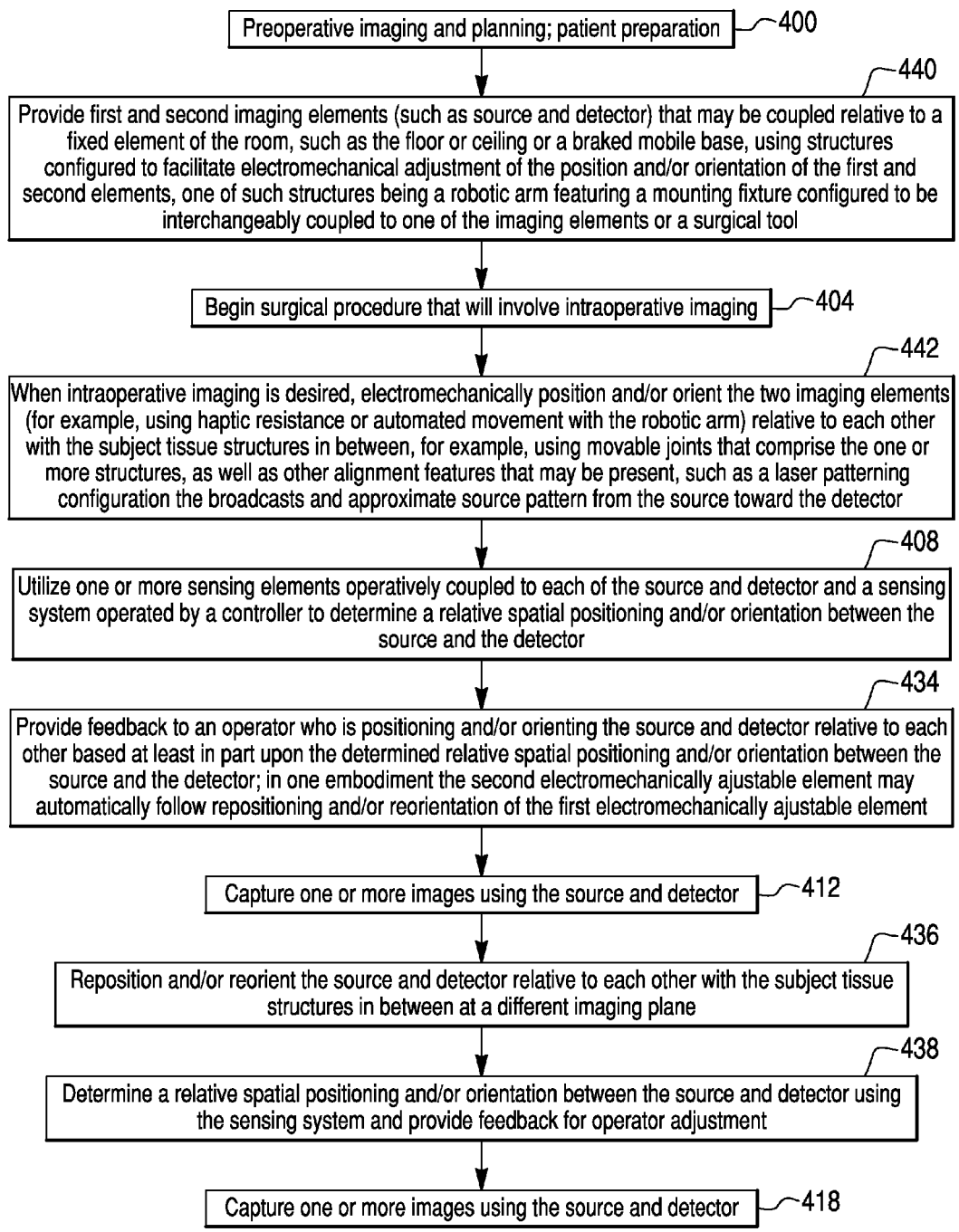

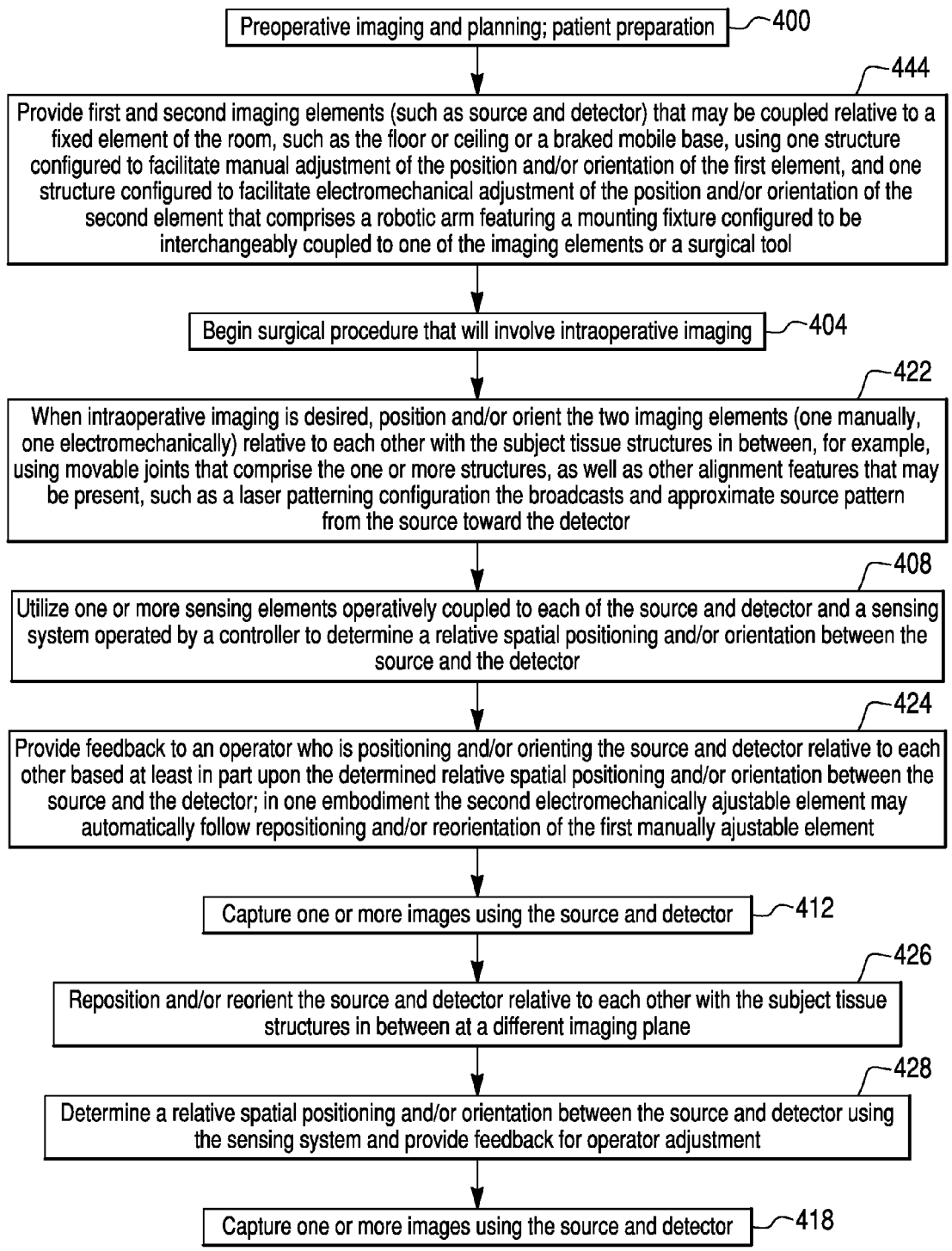

SYSTEM FOR IMAGE-BASED ROBOTIC SURGERY

CROSS-REFERENCE TO RELATED PATENT APPLICATIONS

This application is a continuation of U.S. patent application Ser. No. 13/728,756, filed Dec. 27, 2012, which claims the benefit of and priority to U.S. Provisional Patent Application No. 61/582,145, filed Dec. 30, 2011, both of which are hereby incorporated by reference herein in their entireties.

FIELD

The present invention relates generally to robotic surgery techniques, and more particularly to configurations which may be utilized to efficiently facilitate intraoperative imaging by fluoroscopy during surgical procedures such as joint resurfacing or replacement.

BACKGROUND

With continued surgery-related diagnostic and treatment specialization, and increases in the costs associated with maintaining and staffing operating room space, there is a continued need for capital equipment technologies and configurations that facilitate flexibility and efficiency. For example, radiography and fluoroscopy systems for providing intraoperative images during procedures such as orthopaedic surgery conventionally have comprised relatively large and unwieldly hardware configurations, such as the conventional fluoroscopy C-arm system depicted in FIG. 1A, and the conventional flat-panel radiography system depicted in FIG. 1B which is partially ceiling-mounted and partially floor mounted. Operation of these systems generally requires moving one or more movable portions into a position and/or orientation relative to one or more subject tissue structures of a patient, and often repositioning and/or reorientation to capture additional images from another viewpoint relative to the tissue structures. For example, in the case of many joint arthroplasty related procedures, it will be of interest for the surgeon to gather both antero/posterior and lateral views of the particular skeletal joint of interest, and gathering both views will require movements, either manually or electromechanically induced, of the various portions of imaging hardware. Further, it is sometimes the case that the anatomy of interest of the patient will move during the procedure, potentially requiring re-alignment of the imaging hardware to procure additional intraoperative views. To address the latter problem specifically in a scenario wherein a moving joint is to be imaged during active gait on a treadmill, one university research group has created a system wherein two robotic arms may be utilized to hold an imaging source and detector on opposite sides of a joint of interest and approximately maintain such a relationship while the joint is moved (i.e., as the patient walks on the treadmill). Such a system would not be usable in the tight quarters of an operating room setting, would not be portable (i.e., to facilitate maximum flexibility for the operating room usage scenario), and would require the relatively immense cost of installing and maintaining two robotic arms in the direct vicinity of the operating table. There is a need for a portable, flexible imaging system that facilitates efficient intraoperative imaging in a setting wherein repositioning and/or reorientation of the imaging source and detector relative to the patient anatomy and/or each other is likely required.

SUMMARY

One embodiment is directed to a robotic surgery system, comprising: a mobile base configured to be movable into and out of an operating room when in a freewheeling mode, and fixed relative to the operating room when in a braked mode; a first robotic arm coupled to the mobile base and comprising a mounting fixture configured to be interchangeably coupled to a surgical tool and a first element of a fluoroscopic imaging system comprising a source element and a detector element; a second element of the fluoroscopic imaging system configured to be repositionable relative to a patient tissue structure that may be placed between the first and second elements of the fluoroscopic imaging system; and a controller operatively coupled to the first robotic arm, the controller configured to receive signals from a sensing system operatively coupled to the controller, the sensing system configured to detect motion of one or more sensor elements coupled to each of the first and second elements of the fluoroscopic imaging system and determine a relative spatial positioning between each of the first and second elements of the fluoroscopic imaging system. The first robotic arm may comprise one or more joints and one or more motors configured to controllably regulate motion at the one or more joints. The system further may comprise at least one sensor configured to monitor a position of at least a portion of the first robotic arm. The at least one sensor may be selected from the group consisting of: an encoder, a potentiometer, an optical position tracker, an electromagnetic position tracker, and a fiber bragg deflection sensor. In one embodiment, the first element may be the source element and the second element may be the detector element. In another embodiment, the first element may be the detector element and the second element may be the source element. The source element may be configured to produce a collimated beam having a cross-sectional shape selected from the group consisting of: a circle, an ellipse, a square, and a rectangle. The detector element may be a flat panel detector. The flat panel detector may be an amorphous silicon panel detector. The flat panel detector may be a CMOS fluoroscopy panel. The flat panel detector may have an effective image area having a shape selected from the group consisting of: a circle, an ellipse, a square, and a rectangle. The flat panel detector may comprise a rectangular CMOS active fluoroscopy panel having dimensions of about 5 inches by about 6 inches. The surgical tool may comprise a bone cutting tool. The bone cutting tool may comprise a motor. The bone cutting cool may comprise a bone cutting element selected from the group consisting of: a rotary cutting burr, an insertion/retraction motion reciprocal cutting saw, and a lateral reciprocal motion cutting saw. The mounting feature may comprise a tool chuck configured for manually-facilitated removable coupling of the first element of the fluoroscopic imaging system and the surgical tool. The second element of the fluoroscopic imaging system may be coupled to a movable stand. The movable stand may be electromechanically movable in response to commands input by an operator. The movable stand may be manually movable in response to loads applied by an operator. The movable stand may be mounted to the operating room. The movable stand may be coupled to the mobile base. The sensing system may be selected from the group consisting of: an optical sensing system, an electromagnetic sensing system, a joint rotation sensing system, and an elongate member deflection-sensing system. The one or more sensor elements may be selected from the group consisting of: a reflective marker, an electromagnetic localization sensor, a Bragg grating on an optical fiber, a strain gauge, a joint rotation encoder, and a joint rotation potentiometer. The controller may be configured such that repositioning of the second element causes the robotic arm to reposition the first element to maintain a desired positional alignment between the first and second elements. The controller may be configured such that reorientation of the second element causes the robotic arm to reorient the first element to maintain a desired rotational alignment between the first and second elements. The system further may comprise a user interface configured to allow for an operator to select a desired geometric relationship between the first and second elements relative to the patient tissue structure. The system further may comprise a registration probe that may be removably coupled to the mounting fixture and used to register structures within reach of the probe to the coordinate system of the robotic arm.

BRIEF DESCRIPTION OF THE DRAWINGS

FIG. 3 depicts an intraoperative imaging embodiment in accordance with the present invention in a knee lateral view configuration, wherein both a first and second imaging element are supported by manually movable stands that are coupled to a fixed, or temporarily fixed, structure such as an operating table.

FIG. 4 depicts an intraoperative imaging embodiment in accordance with the present invention in a knee lateral view configuration, wherein both a first and second imaging element are supported by manually movable stands that are coupled to a fixed, or temporarily fixed, structure such as a mounting stem coupled to a movable base with braked wheels.

FIG. 10 is a flow diagram of a process for using an intraoperative imaging embodiment in accordance with the present invention.

FIG. 11 is a flow diagram of a process for using an intraoperative imaging embodiment in accordance with the present invention with an electromechanically adjustable image pair element mounting structure paired with a manually-adjustable structure.

FIG. 12 is a flow diagram of a process for using an intraoperative imaging embodiment in accordance with the present invention with two electromechanically adjustable image pair element mounting structures.

FIG. 13 is a flow diagram of a process for using an intraoperative imaging embodiment in accordance with the present invention with two electromechanically adjustable image pair element mounting structures, one of which is a robotic arm featuring a mounting fixture.

FIG. 14 is a flow diagram of a process for using an intraoperative imaging embodiment in accordance with the present invention with an electromechanically adjustable image pair element mounting structure that is a robotic arm featuring a mounting fixture.

DETAILED DESCRIPTION

Figure 1A:
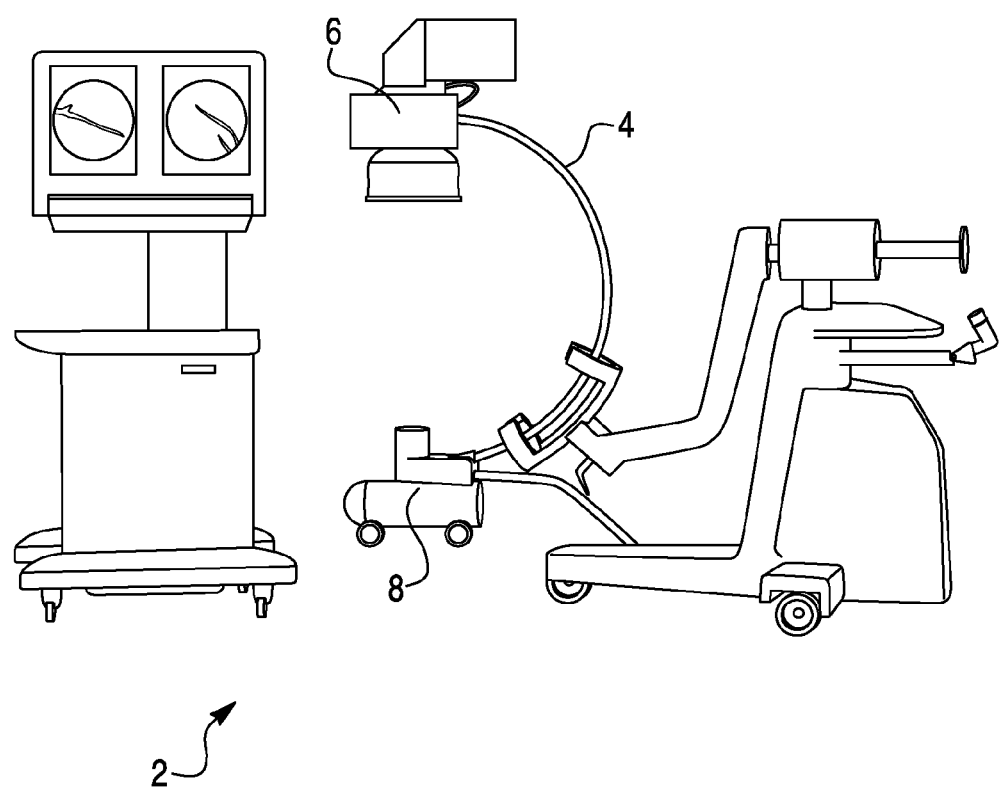
FIG. 1A depicts a conventional fluoroscopic imaging system with a C-arm coupling a source and a detector.
Figure 1B:
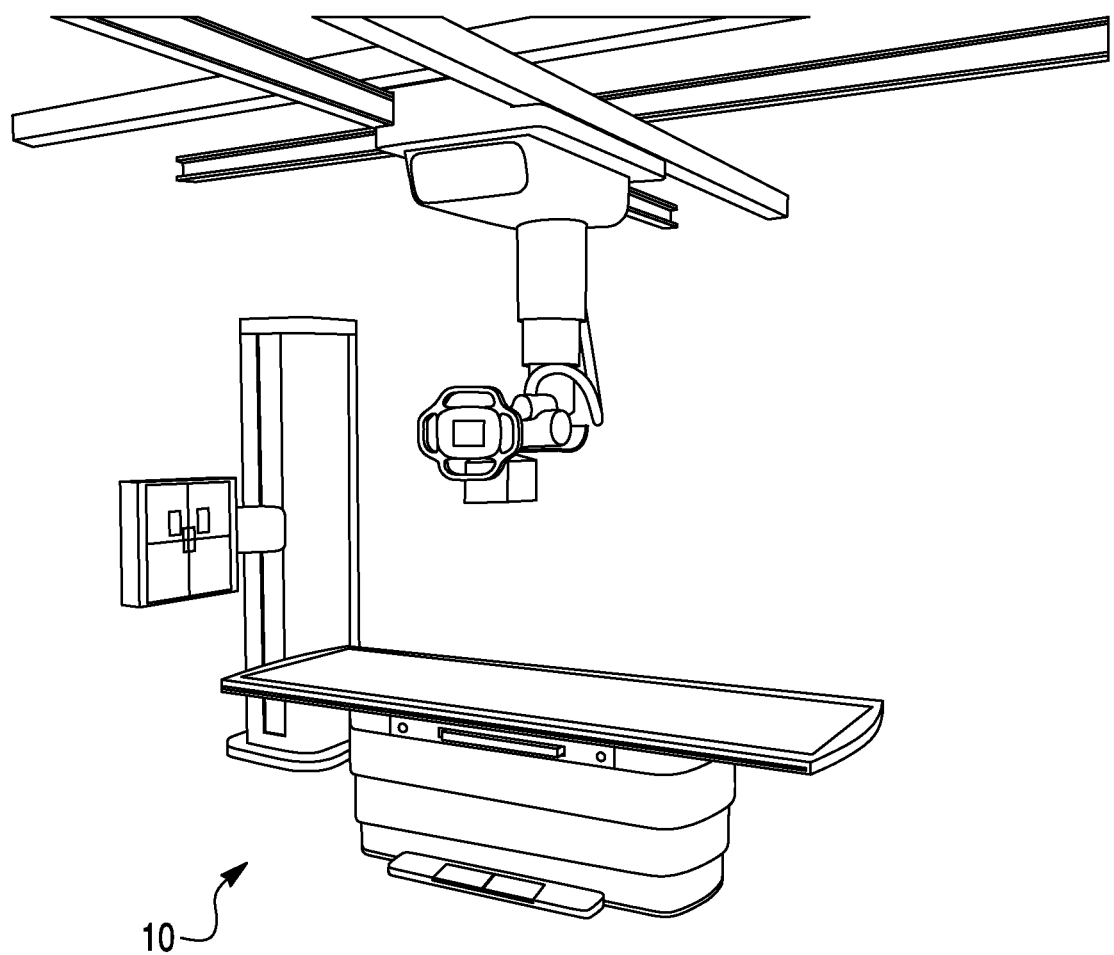
FIG. 1B depicts a conventional radiographic imaging system with a flat panel detector.
Figure 2A:
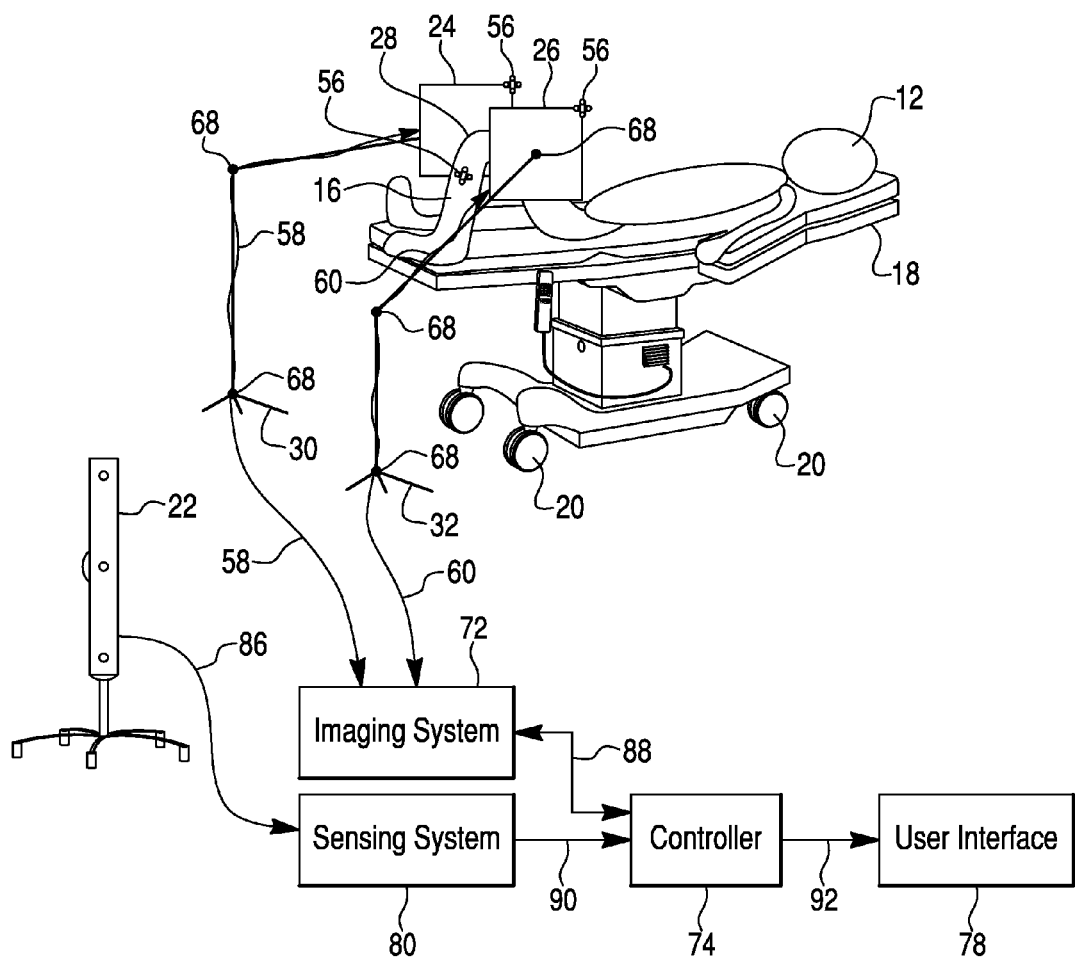
FIG. 2A depicts an intraoperative imaging embodiment in accordance with the present invention in a knee lateral view configuration, wherein both a first and second imaging element are supported by manually movable stands.

Referring to FIG. 2A, one embodiment of a flexible and mobile intraoperative imaging configuration is illustrated. A patient (12) is shown on an operating table (18) that is supported by a movable base having braked wheels (20; in other words, wheels that can be controllably placed in a locked or fixed position to temporarily fix the operating table relative to the floor of the operating room). Two fluoroscopic imaging elements are shown with similar appearance (24, 26); these represent a matched pair of a fluoroscopic imaging source, and a fluoroscopic imaging detector, and may be interchangeably switched in position with each other (i.e., so long as the source is appropriately oriented toward the detector, it generally does not matter which side of the tissue structure of interest, here the knee (28), the source element lies on relative detector element). In the depicted embodiment, the first (24) and second (26) fluoroscopic imaging elements are set up to produce a lateral knee joint image; referring to FIG. 2B, the first (24) and second (26) fluoroscopic imaging elements are set up to produce an anteroposterior knee joint image. Each of the first (24) and second (26) fluoroscopic imaging elements has an electronic lead (58, 60 respectively) operatively coupling the elements (24, 26) to fluoroscopic imaging system (72), such as those sold by the Medical Systems division of General Electric, which is shown operatively coupled (88) to a controller (74) such as a computing workstation, which is shown operatively coupled (92) to user interface (78) such as a monitor and/or input device such as a keyboard. Also operatively coupled

Figure 2B:
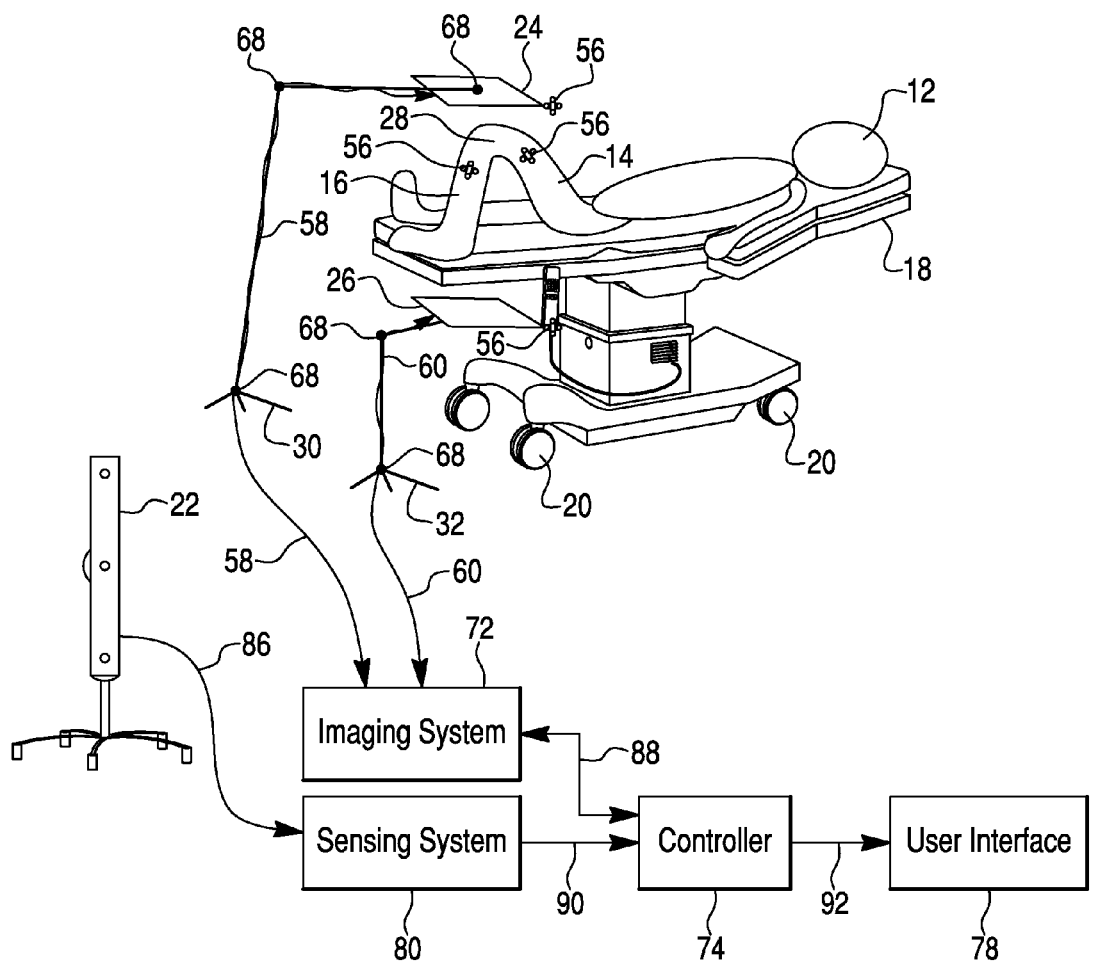
FIG. 2B depicts an intraoperative imaging embodiment in accordance with the present invention in a knee anteroposterior view configuration, wherein both a first and second imaging element are supported by manually movable stands.

(90) to the controller (74) via an electronic lead is an optical sensing system (80) that receives input and sends commands via its connection (86) with an optical tracking transceiver (22), such as those sold by Northern Digital Corporation. The optical tracking transceiver (22) is located such that it is capable of tracking marker arrays (56) that may be fixedly coupled to structures that are to be tracked, such as the two imaging elements (24, 26), and the femur (14) and tibia (16) of the patient (12) in the depicted embodiment. In the embodiments of FIGS. 2A and 2B, the imaging elements (24, 26) are supported relative to each other and the subject tissue structure by first and second movable stands (30, 32), which are configured to stand solidly on the floor of the operating room, and to have manually releasable joints (68), such as spherical or compound joints, or slidable joints for length adjustment, which may be released to manually adjust the position and/or orientation of the imaging elements (24, 26) relative to each other or relative to the subject tissue structure to be imaged, here the knee (28) of the patient (12).

In operation, an operator or user of the system embodiment depicted in FIGS. 2A and 2B has the ability to geometrically characterize the positions and rotations of the imaging elements (24, 26) and tissue structures such as the femur (14) and tibia (16) of the patient (12) which may be the subject of the diagnostic and/or interventional procedure. In one configuration, a relatively low-power laser beam may be scanned about (using a mirror mounted to a high frequency galvanometer, for example) from the source element side of the imaging element pair to provide an aiming reticle that simulates the path of the source radiation toward the detector. This aiming reticle may be used to assist the operator in positioning and orienting the source side of the imaging element pair relative to the anatomy using the manually movable stand features. With the source side of the imaging element pair in place, the operator may utilize feedback from the optical sensing system (80), along with control software on the controller (74) and user interface (78) to manually move the detector side element of the imaging pair into alignment with the source side and the anatomy of interest, to ensure rotational and positional alignment of the pair (for image quality, and also to prevent any unneeded radiation overshoot that is not usable via the detector element for creating an image). The user interface (78) may be configured to present a two or three dimensional guidance display to assist the operator in quickly and efficiently aligning the imaging element pair (24, 26) with each other and the anatomy; the user interface (78) may be further configured to provide audio signals indicative of "docking" into alignment, or proximity thereto (for example, a tone that increases in frequency and ultimately beeps intermittently when alignment is achieved within a predetermined tolerance). Preferably a switch from lateral view to another common imaging view, such as an antero-lateral view as shown in FIG. 2B, is made relatively easy and efficient with the depicted system, since the imaging element pair (24, 26) may be repositioned and reoriented relative to each other and the subject anatomy by simply manually maneuvering the movable stands (30, 32) and going through an alignment procedure as described above, followed by capture of one or more images.

Referring to FIG. 3, an embodiment similar to that of FIG. 2A is depicted, with exception that the first and second fluoroscopic imaging element (24, 26) stands (36, 38) are coupled to the operating table (18) or other nearby sturdy mechanical element that is generally fixable relative to the global coordinate system of the operating floor. Such a configuration has individual leads (58, 60) to/from the imaging elements which may be joined into a common lead or conduit (62) to reach the fluoroscopic imaging system (72). The resultant footprint of this embodiment in the operating room is relatively efficient, and in operation, similar steps apply as have been described above in reference to FIGS. 2A and 2B.

For illustrative purposes, the embodiment of FIG. 4 features several other modalities for tracking the positions and/or orientations of various structures comprising the system (many modalities may be used separately or combined, including optical tracking techniques as described above, electromagnetic localization techniques (such as those described and offered by the Biosense division of Johnson & Johnson, Inc), joint encoder or potentiometer angle reading and aggregation techniques (such as those used in many articulated robots, wherein simple geometry is applied along with angle readings at joints to determine positions and orientations of structures in three-dimensional space), and fiber-Bragg shape sensing and localization techniques, such as those described and offered by Luna Innovations, Inc), in addition to optical tracking as described above in reference to FIGS. 2A-2B and FIG. 3. Further, the embodiment of FIG. 4 features a common mounting stem (46) fixedly coupled to a mobile base (44) having braked wheels (20) to be temporarily fixed relative to the operating room floor (98) and a global coordinate system (100) that may be associated thereto.

Referring to FIG. 4, many tracking options are presented. For example, the movable base (44) may be tracked using the optical tracking system (80) using one or more marker arrays (56) fixedly coupled to the movable base (44), so that the mobile base coordinate system (102) may be geometrically defined relative to the global coordinate system (100). The tibia (16) and femur (14) may also be optically tracked using one or more marker arrays (56) fixedly coupled thereto (i.e., using bone screws, k-wire, Steinman pins, relatively firm bracing constructs coupled around the skin surface, or the like). In this embodiment, the first fluoroscopic imaging pair element (24) is tracked in space using a group of electromagnetic localization sensors (108) coupled to the element (24) and coupled via electronic leads (112) back to an electromagnetic transducer subsystem (106) (and a coordinate system (104) associated therewith), which is coupled by electronic lead (113) back to the electromagnetic localization and sensing system (82), which is operatively coupled (94) to the controller. Finally, a Bragg grating fiber (110) is utilized in the depicted illustrative embodiment to show that fiber Bragg shape sensing and/or localization techniques may also be utilized to characterize the position and/or orientation of one or more elements of the system in space relative to a coordinate system such as the mobile base coordinate system (102). The Bragg fiber (110) leads back to the fiber Bragg ("FBG") sensing system (84), which may be operatively coupled (96) to the controller (74). Strain gauges and structures containing them may also be utilized to monitor the positions of various elements. Thus a variety of position and/or orientation sensing means may be applied to assist in characterizing the elements of the system so that the controller (74) and user interface (78) may be utilized to guide an operator through easy, efficient alignment of source and detector elements for imaging purposes.

Figure 5:
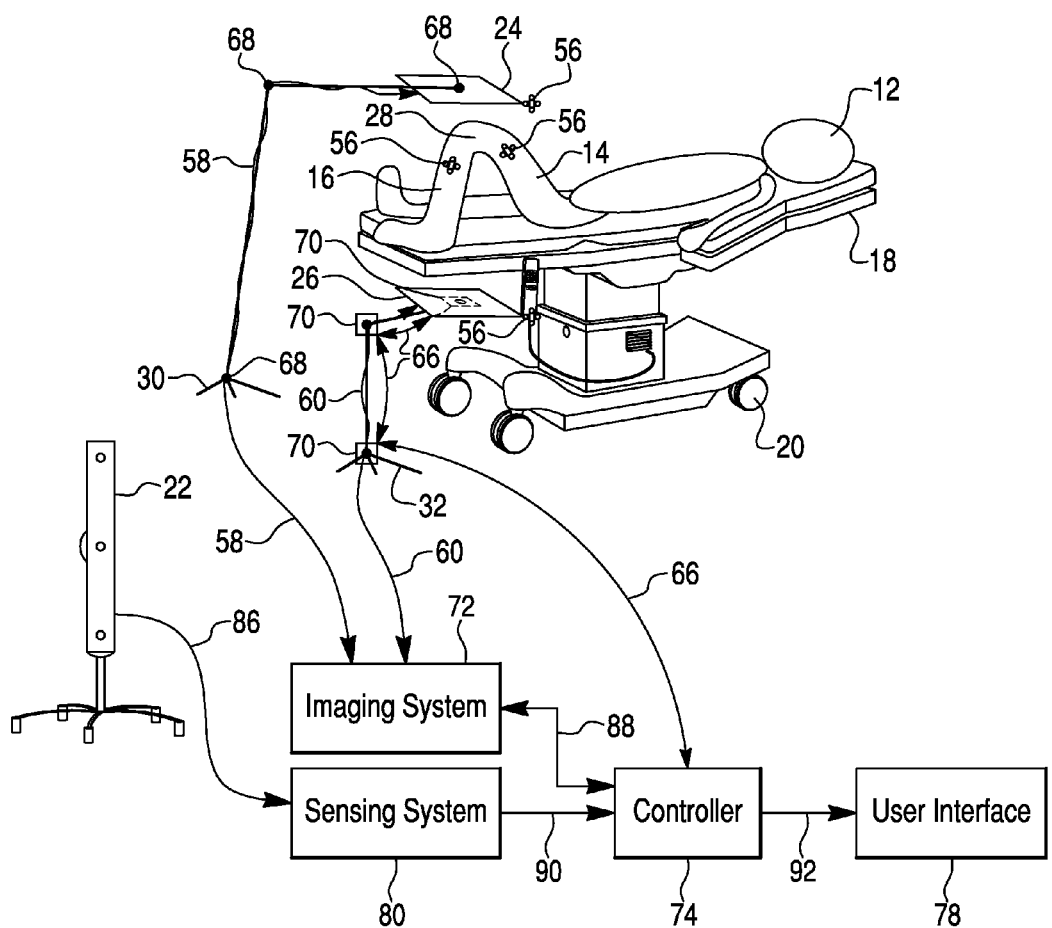
FIG. 5 depicts an intraoperative imaging embodiment in accordance with the present invention in a knee anteroposterior view configuration, wherein both a first and second imaging element are supported by movable stands, one of which is manually movable and the other of which is electromechanically movable.

Referring to FIG. 5, an embodiment similar to that of FIG. 2B is shown, with the addition of electromechanically movable joints (70—symbolized as a square around a circle) on one of the movable stands (32). A joint actuation control lead (66) couples the various electromechanically movable joints (70) back to the controller (74) so they may be controllably actuated, braked, and the like. In one embodiment, a configuration such as that depicted in FIG. 5 may be utilized such that an operator manually places the non-electromechanical stand (30) into a desired position (say, for example, that the first imaging element (24) associated with this first stand is the source element, and that it may be conveniently aimed with the assistance of an aiming laser beam configuration as described above), and the controller automatically and electromechanically places the second imaging element into a predetermined alignment relative to the anatomy and the first imaging element, such as in an alignment that ensures orthogonal positioning and no roll angle between source and detector. In another embodiment, the electromechanically movable joints (70) may be utilized to haptically guide the electromechanically-actuated stand (32) into a predetermined desired position (i.e., under the power/urging force of an operator, but along a path that is haptically enforced using the motors of the electromechanically-actuated stand (32)).

Figure 6:
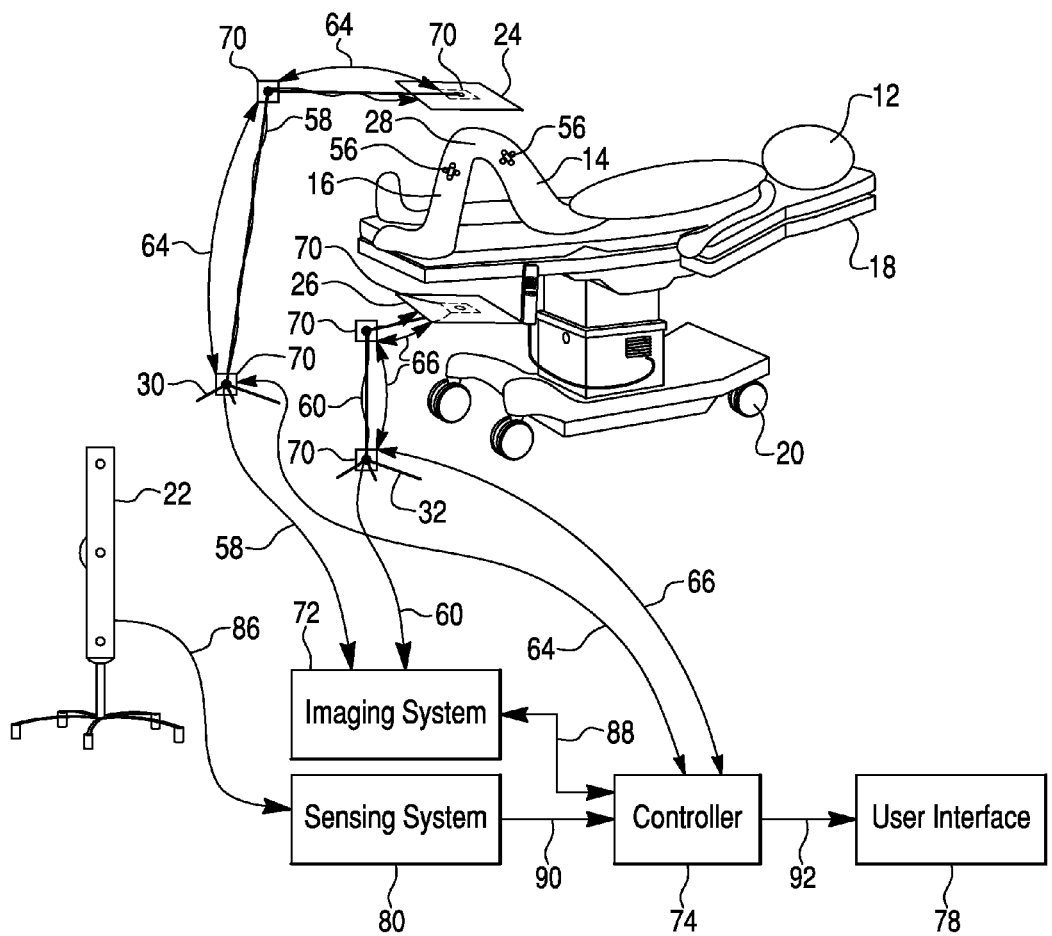
FIG. 6 depicts an intraoperative imaging embodiment in accordance with the present invention in a knee anteroposterior view configuration, wherein both a first and second imaging element are supported by movable stands, both of which are electromechanically movable.

Referring to FIG. 6, an embodiment is shown wherein both of the stands (30, 32) have electromechanical joints (70) that may be controlled precisely by the controller. The leads for controlling the joints are denoted by elements 64 and 66, as shown in FIG. 6. Preferably the joints have encoders, potentiometers, or other sensors to assist with the control paradigm of the stand elements (i.e., such as forward kinematics, closed loop control, etc). With such a configuration, the controller (74) may be programmed to allow an operator to overcome a stabilizing/fixating braking force to move one of the stands into a new position, and subsequently move the opposite stand into a desired orientation relative to the stand that was manually manipulated. For example, with such a configuration, the operator could pull the first stand (30) from a previous lateral view imaging plane configuration into a configuration wherein a laser aiming beam appears to provide a desirable antero-posterior view, and the second stand (32) could immediately and automatically follow to position/orient itself in a desirable opposite position to complete the antero-posterior imaging view (or in another embodiment wherein automated motion is not as desirable, the second stand (32) could lend itself to haptically-guided repositioning to complete the antero-posterior imaging view).

Figure 7:
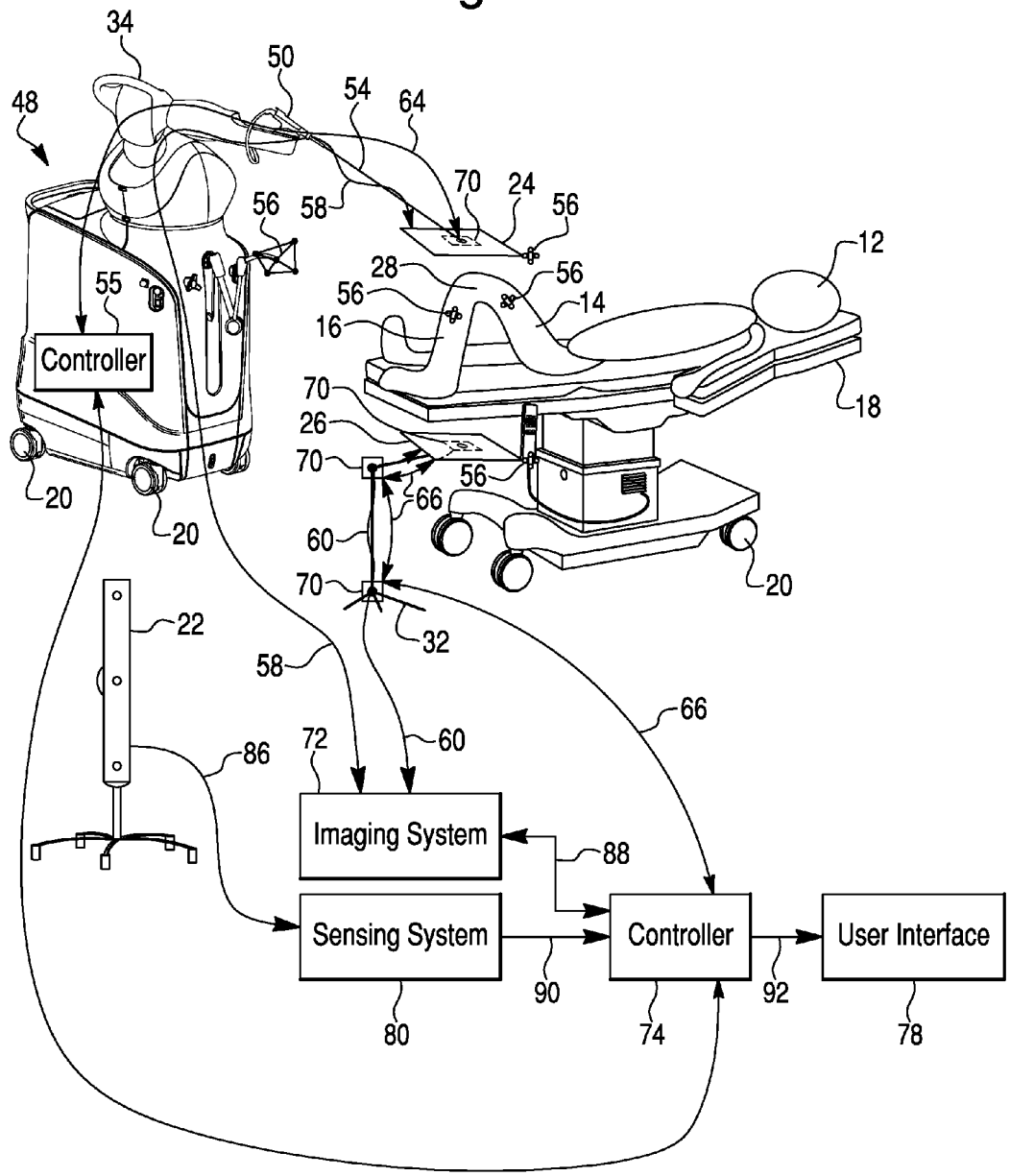
FIG. 7 depicts an intraoperative imaging embodiment in accordance with the present invention in a knee anteroposterior view configuration, wherein both a first and second imaging element are supported by movable stands, both of which are electromechanically movable, and one of which is a robotic arm comprising a portion of a robotic surgery system.

Referring to FIG. 7, an embodiment similar to that of FIG. 6 is depicted, with a robotic surgery system (48), such as that available from MAKO Surgical Corp. under the tradename RIO® functioning in the place of one of the electromechanical stands (30) that was shown in FIG. 6. The surgery system (48) has its own on-board controller (55), a mobile base with braked wheels (20), and comprises a sophisticated robotic arm (34) that may be utilized for precision affirmative navigation or haptic-guidance for manually-powered navigation of tools that may be coupled to a mounting fixture (50) configured not only to mount an imaging element manipulation tool (54) as shown, but also a surgical tool, such as a bone cutting tool, which may be utilized in the procedure. The mounting fixture (50) or the tool itself may comprise a motor. Bone cutting tools may comprise one or more bone cutting elements, such as a rotary cutting burr, an insertion/retraction motion reciprocal saw, and/or a lateral motion cutting saw. An optical sensor element or array (56), such as one containing one or more reflective spheres, discs, or other shapes, may be fixedly attached to the robotic surgery system (48) for tracking it, and a probe tool (not shown) may be mounted to the mounting fixture (50) to register the tip of the robotic arm (34) to other pertinent structures or coordinate systems, such as those of the patient anatomy, the other imaging element to a pair, etc. Using a highly sophisticated robotic arm such as that depicted as part of the robotic surgery system (48) may seem like too much technology and/or expense for orienting one half of an imaging element pair, but in a procedure wherein the system is going to be utilized anyway (such as one wherein the RIO® system is to be utilized to resurface a skeletal joint of a patient), the interchangeable mounting fixture (50) or tool chuck facilitates an opportunity to use the technology for the imaging aspect of the procedure as well.

Figure 8:
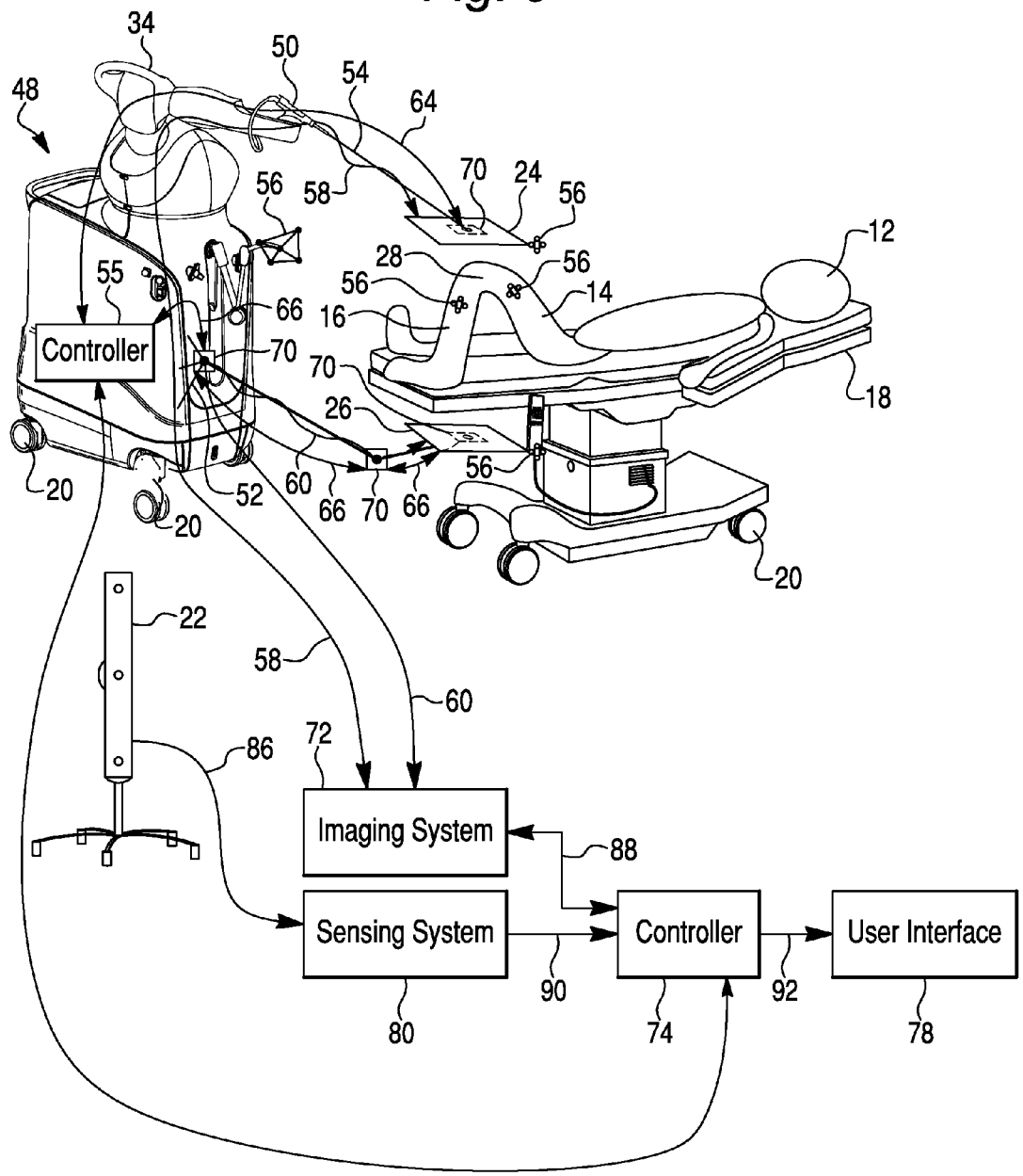
FIG. 8 depicts an intraoperative imaging embodiment in accordance with the present invention in a knee anteroposterior view configuration, wherein both a first and second imaging element are supported by movable stands, both of which are electromechanically movable, and one of which is a robotic arm comprising a portion of a robotic surgery system.
Figure 9:
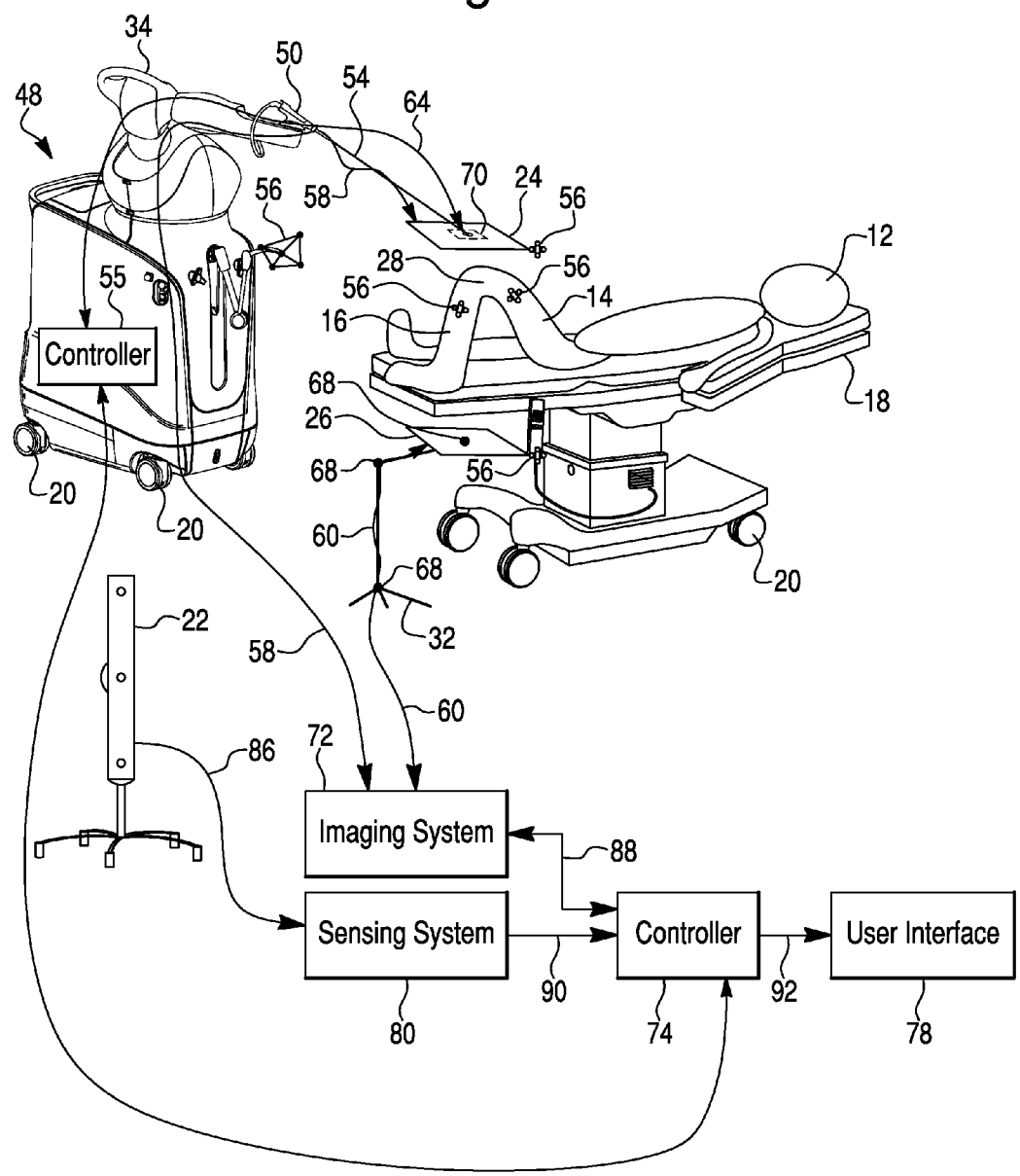
FIG. 9 depicts an intraoperative imaging embodiment in accordance with the present invention in a knee anteroposterior view configuration, wherein both a first and second imaging element are supported by movable stands, one of which is manually movable, and the other of which is a robotic arm comprising a portion of a robotic surgery system.

Referring to FIG. 8, an embodiment similar to that of FIG. 7 is illustrated, with the second electromechanically-actuated imaging element stand structure (52) proximally fixedly mounted to the robotic surgery system (48) to reduce the overall system footprint and physically organize both sides of the imaging element pair from the ground up starting with as many common structures as possible to reduce errors in calculating the relative positioning and orientation of the imaging elements relative to each other.

Referring to FIG. 8, an embodiment similar to that of FIG. 7 is illustrated, with exception that the second imaging pair element stand (32) is a simple manually-movable configuration, as shown, for example, in FIGS. 2A and 2B. In one embodiment, the second imaging element (26) coupled to the manually movable stand (32) may be manually pulled into a position or orientation (i.e., by temporarily loosening or unlocking the manual joints 68), and the robotic arm (34) may be configured to automatically follow this action by placing the first imaging element (24) in a desired related position or orientation—or allow for haptic guidance to such desired related position or orientation under the power of the operator's own manual loads.

Again, many configurations and combinations of stands, sensing modalities, sensors, and control configurations may be utilized within the scope of this invention to facilitate high-efficiency and high-quality fluoroscopy intraoperatively. Various elements may be fixedly and/or removably mounted to the ceiling of the operating room as opposed to, or in addition to, mounting configurations to the floors or other structures as shown. The source element of the imaging element pair preferably will produce a collimated beam having a cross-sectional shape that is circular, elliptical, square, or rectangular—and preferably a detector will be matched to have an effective image area that has a circular, elliptical, square, or rectangular shape. Preferably the detector element will be a flat panel detector, such as those characterized as amorphous silicon detectors or CMOS flat panel detectors. In one embodiment, a relatively low-inertia rectangular flat panel of dimensions approximately 5 inches by 6 inches may be utilized with a relatively low inertia source that may be designed for dentistry or hand-held use, such as those available from Aribex, Inc. Preferably the detector will be capable of a "continuous acquisition mode" to facilitate real-time, or near-real-time, continuous imaging. In another embodiment, the detector may be configured to handle one image acquisition at a time, in a mode known as "digital radiography".

Referring to FIGS. 10-14, various techniques for utilizing embodiments such as those described in reference to FIGS. 2A-9 are illustrated.

Referring to FIG. 10, subsequent to preoperative imaging, planning, and patient preparation (400), imaging source and detector elements may be provided and mounted upon manually-adjustable structures (402). After the procedure has begun (404) and intraoperative imaging is desired (406), the manually-adjustable structures may be positioned and oriented relative to each other using movable joints, in some embodiments using an alignment assistance feature such as a source pattern simulator such as a laser pattern. Controllably bendable, stretcheable, or otherwise deformable structures may also be utilized subject to the ability to characterize the positioning and orientation of the imaging elements. Sensing elements may be operatively coupled (408) to the imaging elements and configured to be utilized by a sensing system to characterize relative spatial positioning and/or orientation of the imaging elements relative to each other, and relative to other important structures, such as the tissue structures to be imaged. Feedback may be provided (410) to an operator to assist with positioning and/or orientation alignment of the imaging elements and anatomy. With everything aligned, one or more images may be captured (412) using the source and detector imaging elements. Subsequently, the source and detector elements may be repositioned and/or reoriented to provide a different imaging plane, for example (414), and the sensing configuration may be utilized to assist the operator and provide feedback as above (416), followed by image acquisition at the new position and/or orientation (418).

Referring to FIG. 11, an embodiment similar to that of FIG. 10 is illustrated, with the exception that the embodiment of FIG. 11 incorporates use of one electromechanically adjustable image pair element mounting structure (420) paired with the other manually-adjustable structure. One of the imaging elements (i.e., either source or detector) may be positioned electromechanically (422, 424)—either automatically using one or more motors that are operatively coupled to the pertinent joints of the structure, or via haptic guidance provided through one or more operatively coupled motors that are configured to allow the operator to move the structure with his own might, but to guide the path and geometry using electromechanical haptics. After capturing one or more images (412), the electromechanical assistance may be used again (426, 428) for an additional image acquisition (418).

Referring to FIG. 12, an embodiment similar to that of FIG. 11 is illustrated, with the exception that the embodiment of FIG. 12 incorporates use of two electromechanically adjustable image pair element mounting structures (430). Both elements may be positioned and/or oriented electromechanically (432, 434), followed by image acquisition (412), repeated positioning and/or reorientation electromechanically (436, 438), and further image acquisition (418).

Referring to FIG. 13, an embodiment similar to that of FIG. 12 is illustrated, with the exception that the embodiment of FIG. 13 incorporates use of two electromechanically adjustable image pair element mounting structures, one of which is a robotic arm featuring a mounting fixture that may be used for imaging as well as one or more surgical tools (440, 442).

Referring to FIG. 14, an embodiment similar to that of FIG. 11 is illustrated, with the exception that the embodiment of FIG. 14 incorporates use of one electromechanically adjustable image pair element mounting structure that is a robotic arm featuring a mounting fixture that may be used for imaging as well as one or more surgical tools (444).

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A robotic surgery system, comprising:
a robotic arm coupled to a base fixed relative to an operating room, wherein the robotic arm comprises a mounting fixture configured to be coupled to a first element of a fluoroscopic imaging system comprising a source element and a detector element, wherein the first element is one of the source element and the detector element;
a second element of the fluoroscopic imaging system, wherein the second element is the other of the source element and the detector element, the second element configured to be repositionable relative to the first element of the fluoroscopic imaging system and relative to a patient tissue structure such that the patient tissue structure may be positioned between the first and second elements of the fluoroscopic imaging system;
a controller operatively coupled to the first robotic arm, the controller configured to receive signals from a sensing system operatively coupled to the controller, the sensing system configured to detect motion of one or more sensor elements coupled to each of the first and second elements of the fluoroscopic imaging system and determine a relative spatial positioning between each of the first and second elements of the fluoroscopic imaging system; and
a user interface configured to allow for an operator to select a desired geometric relationship between the first and second elements relative to the patient tissue structure.

2. The system of claim 1, wherein the robotic arm is coupled to a base that is fixed to a ceiling of the operating room, a floor of the operating room, or an operating table.

3. The system of claim 1, wherein the robotic arm is coupled to a base that is removably mounted to a ceiling of the operating room.

4. The system of claim 1, wherein the robotic arm is coupled to a base that is fixedly mounted to a ceiling of the operating room.

5. The system of claim 1, wherein the robotic arm comprises one or more joints and one or more motors configured to controllably regulate motion at the one or more joints.

6. The system of claim 5, wherein the one or more motors are configured to provide haptic guidance to the robotic arm.

7. The system of claim 1, further comprising at least one sensor configured to monitor a position of at least a portion of the robotic arm, the at least one sensor selected from the group consisting of: an encoder, a potentiometer, an optical position tracker, an electromagnetic position tracker, and a fiber bragg deflection sensor.

8. The system of claim 1, wherein the source element is configured to produce a collimated beam having a cross-sectional shape selected from the group consisting of: a circle, an ellipse, a square, and a rectangle.

9. The system of claim 1, wherein the detector element is a flat panel detector selected from the group consisting of: an amorphous silicon panel detector and a CMOS fluoroscopy panel.

10. The system of claim 9, wherein the flat panel detector has an effective image area having a shape selected from the group consisting of: a circle, an ellipse, a square, and a rectangle.

11. The system of claim 1, wherein the mounting fixture is configured to be interchangeably coupled to a surgical tool and the first element of the fluoroscopic imaging system.

12. The system of claim 11, wherein the surgical tool comprises a bone cutting tool.

13. The system of claim 12, wherein the bone cutting tool comprises motor.

14. The system of claim 12, wherein the bone cutting cool comprises a bone cutting element selected from the group consisting of: a rotary cutting burr, an insertion/retraction motion reciprocal cutting saw, and a lateral reciprocal motion cutting saw.

15. The system of claim 11, wherein the mounting feature comprises a tool chuck configured for manually-facilitated removable coupling of the first element of the fluoroscopic imaging system and the surgical tool.

16. The system of claim 1, wherein the second element of the fluoroscopic imaging system is coupled to a movable stand.

17. The system of claim 1, wherein the sensing system is selected from the group consisting of: an optical sensing system, an electromagnetic sensing system, a joint rotation sensing system, and an elongate member deflection-sensing system.

18. The system of claim 1, wherein the one or more sensor elements are selected from the group consisting of: a reflective marker, an electromagnetic localization sensor, a Bragg grating on an optical fiber, a strain gauge, a joint rotation encoder, and a joint rotation potentiometer.

19. The system of claim 1, wherein the controller is configured such that repositioning of the second element causes the robotic arm to reposition the first element to maintain a desired positional and rotational alignment between the first and second elements.

* * * * *